United States Patent [19]
Kuroda et al.

[11] Patent Number: 5,256,573
[45] Date of Patent: Oct. 26, 1993

[54] METHOD FOR DILUTING AND MIXING LIQUID SPECIMEN

[75] Inventors: Toshiaki Kuroda, Takasagoshi; Hiroyuki Inoue, Kakogawashi, both of Japan

[73] Assignee: Toa Medical Electronics Co., Ltd., Kobe, Japan

[21] Appl. No.: 822,896

[22] Filed: Jan. 21, 1992

[30] Foreign Application Priority Data

Apr. 24, 1991 [JP] Japan .................. 3-122553
Aug. 9, 1991 [JP] Japan .................. 3-224615

[51] Int. Cl.$^5$ .................. G01N 1/10; G01N 1/18
[52] U.S. Cl. .................. 436/179; 436/174; 436/180; 436/54; 422/81; 422/100; 422/103; 73/863.84; 73/863.83; 73/863.81; 73/864.35
[58] Field of Search .......... 436/179, 180, 174, 52–54; 422/81, 82, 100, 103; 222/71; 73/863.73, 863.84, 864.11, 864.12, 864.15, 864.35, 863.83, 863.81

[56] References Cited

U.S. PATENT DOCUMENTS

| | | | |
|---|---|---|---|
| 3,306,111 | 2/1967 | Ferrin | 73/863.73 |
| 3,567,390 | 3/1971 | Rothermel | 422/103 |
| 3,991,055 | 11/1976 | Godin et al. | 436/180 |
| 4,244,919 | 1/1981 | Chen | 222/71 |
| 4,624,928 | 11/1986 | Qureshi | 436/179 |
| 4,810,659 | 3/1989 | Higo et al. | 436/180 |
| 4,873,057 | 10/1989 | Robertson et al. | 422/75 |
| 5,094,961 | 3/1992 | del Valle et al. | 436/180 |
| 5,108,928 | 4/1992 | Menard et al. | 422/82 |

Primary Examiner—James C. Housel
Assistant Examiner—Long Y. Le
Attorney, Agent, or Firm—Jones, Tullar & Cooper

[57] ABSTRACT

A method for diluting and mixing specimen such as blood and a reagent, which is designed to prepare a mixed solution of a specimen and a reagent at a specific ratio by discharging the reagent in a passage for quantitative determination in a sampling valve by a specified amount of the reagent. The method is such that specimen is discharged by reagent first at a low speed and thereafter at a usual speed by a reagent discharge device. The reagent discharge device may comprise a syringe, a pump having a thin film for forming air and liquid chambers, or the like. As constructed, the specimen is not damaged due to fluid pressure.

1 Claim, 8 Drawing Sheets

METHOD FOR DILUTING AND MIXING LIQUID SPECIMEN

CROSS REFERENCE TO RELATED APPLICATION

This application is the parent application of divisional application, Ser. No. 07/913,455, filed Jul. 15, 1992.

BACKGROUND OF THE INVENTION

The present invention relates to a method and apparatus for diluting and mixing a liquid specimen (for example, blood) and a reagent.

In a specimen analyzing apparatus such as a blood analyzer, a sampling valve is used to obtain a specific volume of specimen. The mechanism of a sampling valve is explained below with reference to FIG. 1. Numeral 10 refers to a sampling valve. Numerals 12, 16 refers to fixed elements, and 14 to a movable element enclosed by the fixed elements 12, 16.

The movable element 14 has a penetration passage P2 for quantitative determination (hereinafter called passage P2 or passage P2 for determination). The movable element 14 moves on the fixed elements (linear reciprocal motion or normal and reverse rotary motion). Accordingly, the sampling valve 10 forms a first state and a second state. The first state is the suction mode for sucking or asperating specimen into the sampling valve. The second state is the transfer mode for pushing out or delivering the measured specimen by the liquid from outside.

FIG. 1 shows the first state. The fixed elements 12, 16 are provided with passages P1, P3 which communicate with the passage P2 in the first state. A suction probe (suction capillary) 18 is connected to the passage P1, and a suction means C1 such as a syringe is connected to the passage P3 through a valve V1. Numeral 24 refers to a washing liquid vessel filled with washing liquid, and 20 is a specimen container filled with blood specimen.

The fixed elements 12, 16 have other passages P4, P5. The second state is a state in which the movable element 14 is moved by a specific distance or a specific angle from the first state, and the passage P2 for determination communicates with the passages P4, P5. A reaction vessel 22 is connected to the passage P4 so as to induce reaction between the specimen and the reagent, and a discharge means C2 such as a syringe is connected to the passage P2 through a valve V2. Numeral 26 refers to a reagent vessel containing a reagent for reaction for mixing with the blood specimen, and vessel 26 connected to the passage P5 through a reagent line 27 having the valve V2.

As the suction means C1 operates to suck in or aspirate in the first state, the specimen in the specimen container 20 is charged to fill the passage P2 for determination of the sampling valve 10 via the suction probe 18.

Coming sequentially to the second state, as the discharge means C2 operates to discharge, the specimen in the passage P2 is pushed out together with the reagent to be transferred into the reaction vessel 22, where both are mixed to react. The mixed solution is measured in a measuring unit (not shown).

In a particle counter, for example, to count leukocytes in the blood, it is necessary to destroy erythrocytes. Hitherto, accordingly, a small amount of hemolyzing agent was added to a diluted solution of blood to dissolve the erythrocytes. The hemolyzing agent is, for example, a surface active agent.

However, in the method of adding a small amount of hemolyzing agent to a large volume of specimen suspension, the reaction fluctuates. The hemolyzing agent not only dissolve the erythrocytes but also affects the leukocytes more or less (such as a reduction of size), and hence the effects on leukocytes may also fluctuate. It poses problems when counting by classifying the leukocytes.

To minimize such reaction fluctuations, therefore, consideration has been given to hemolyze and dilute simultaneously in a diluted solution containing a hemolyzing agent. For this purpose, in FIG. 1, the reagent should be a diluted solution containing a hemolyzing agent.

FIG. 2 is a magnified sectional view of the passage part of the sampling valve 10 in the second state (transfer mode). Numeral 28 is a nipple provided in the passage P4 of the fixed element 12, and 30 is a tube connected to the nipple 28. Usually the blood must be diluted several hundred times or more, and the inside diameter of the passage P2 for determination is about 1 mm (or smaller depending on the specification).

When pushing out the specimen in a narrow passage by the liquid from outside in this way, a large fluid pressure acts in this narrow passage. In other words, stress is applied to the blood cells, which may exert some adverse effect or other. Such an effect will not be ignored if the cell membrane of the blood cells is weak due to disease or because it has been left a long time after blood sampling, and when using a liquid reagent that may cause a reaction on the blood cells. Of course, when the reagent is pushed in slowly, the stress will be reduced. But it takes too much time, so that the processing capacity of the analyzing apparatus is lowered.

OBJECT AND SUMMARY OF THE INVENTION

It is hence a primary object of the invention to provide a method and apparatus for diluting and mixing liquid specimen, without lowering the processing capacity of the apparatus and without damaging the specimen by fluid pressure.

To achieve the above object, in one preferred embodiment, the invention provides a method for diluting and mixing specimen by preparing a mixed solution of a specimen and a reagent at a specific ratio including feeding a liquid specimen into a passage for quantitative determination in a sampling valve, changing over the sampling valve, aspirating the specimen in slices, and discharging the specimen with a specific volume of a reagent, wherein the specimen is discharged by the reagent at a low speed until the specimen comes out of the sampling valve, and at a usual speed thereafter.

In this case, "discharging at a low speed" means to discharge at a speed slower than the usual speed.

The invention also provides an apparatus for diluting and mixing specimen comprising a sampling valve for aspirating a liquid specimen in slices, specimen suction means connected to the sampling valve, reagent discharge means and a reaction vessel, thereby preparing a mixed solution of specimen and reagent at a specific ratio, wherein second reagent discharge means which is very slight in discharge capacity, is connected parallel to the reagent discharge means (hereinafter called first reagent discharge means).

In this case, "very slight in discharge capacity" means that the discharge capacity is smaller than in the first reagent discharge means.

The invention moreover provides an apparatus for diluting and mixing specimen comprising a sampling valve for aspirating a liquid specimen in slices, specimen suction means connected to the sampling valve, reagent discharge means and a reaction vessel, thereby preparing a mixed solution of specimen and reagent at a specific ratio, wherein the reagent discharge means comprises a working chamber separated by a thin film into an air chamber and a liquid chamber connected to the reagent line, and further comprises:

a three-way changeover valve connected to the air chamber, a positive pressure supply line connected to the three-way changeover valve, a negative pressure supply line connected to the three-way changeover valve, and a small volume part and a valve disposed in the positive pressure supply line.

Until the specimen comes out of the narrow passage of the sampling valve, it is discharged slowly by the second reagent discharge means, and a large fluid pressure is not applied to the specimen.

Thereafter, it is discharged at a usual speed by the first reagent discharge means. If discharged at high speed, since the inside diameter of the passage is wide, large fluid pressure is not applied to the specimen.

While the three-way changeover valve connected to the air chamber is communicating with the negative pressure side, the liquid chamber of the reagent discharge means is filled with reagent. At this time, the valve installed in the positive pressure supply line is open, and a positive pressure is applied to the small volume part.

Consequently, the valve installed in the positive pressure supply line closed, and a positive pressure accumulates in the small volume part installed between the three-way changeover valve connected to the air chamber and the valve installed in the positive pressure supply line. In sequence, the three-way changeover valve is changed over so that the three-way changeover valve connected to the air chamber may communicate with the positve pressure side. In this way, the positive pressure accumulated in the small volume part is supplied to the air chamber, and for that portion the volume of the air chamber increases slightly, the film is deformed, and a small amount of reagent is slowly discharged from the reagent discharge means.

Afterwards, the valve provided in the positive pressure supply line is open, and the remaining large volume of reagent is discharged at a usual speed.

DESCRIPTION OF THE DRAWINGS

FIG. 7 is a magnified view around the reagent discharge means of FIG. 6, FIG. 8 to FIG. 10 are sectional views showing examples of the reagent discharge means of FIG. 6 and FIG. 7, in which

DETAILED DESCRIPTION OF PREFERRED EMBODIMENTS

Figure 1:
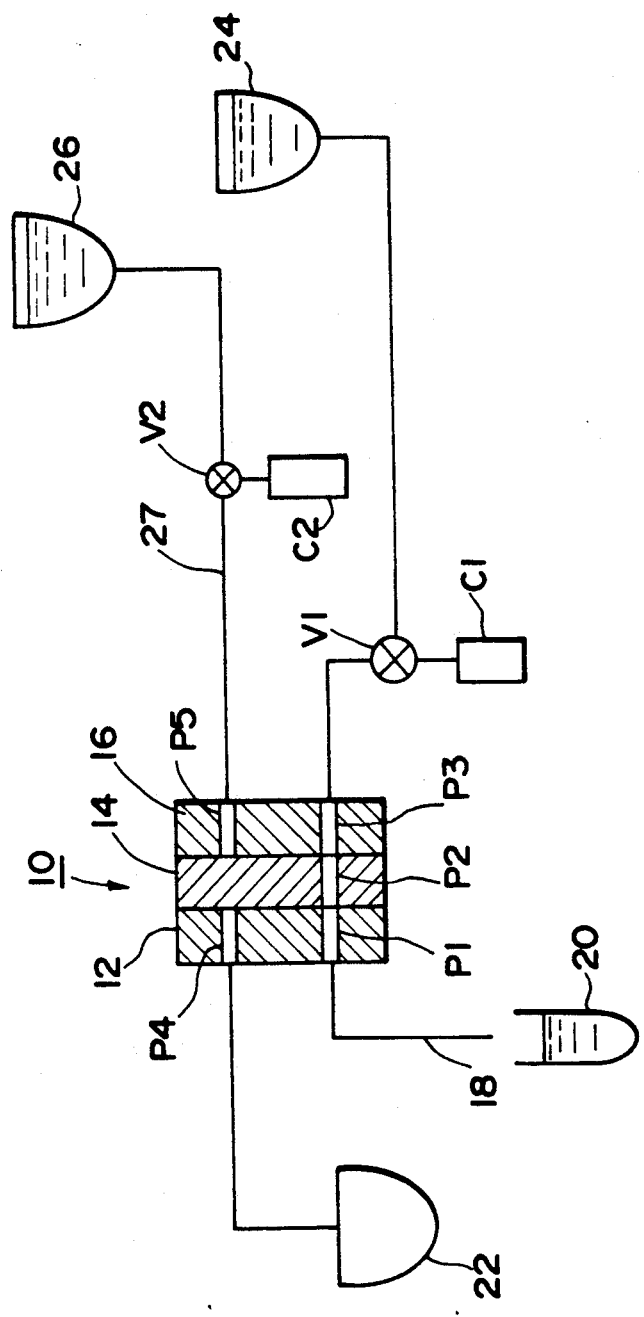
FIG. 1 is a schematic diagram showing a conventional apparatus for diluting and mixing specimen.
Figure 2:
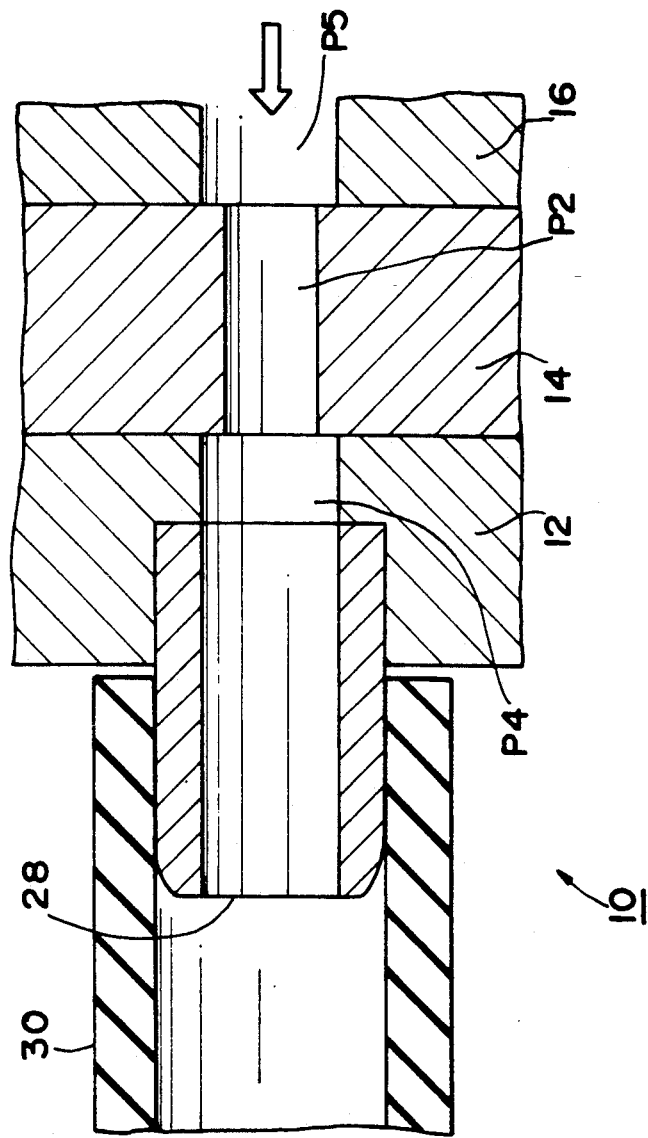
FIG. 2 is a magnified sectional view of the passage part of the sampling valve in a second state (transfer mode) of the apparatus in FIG. 1.

Referring now to the drawings, some of the preferred embodiments of the invention are described in detail below.

EMBODIMENT 1

Figure 3:
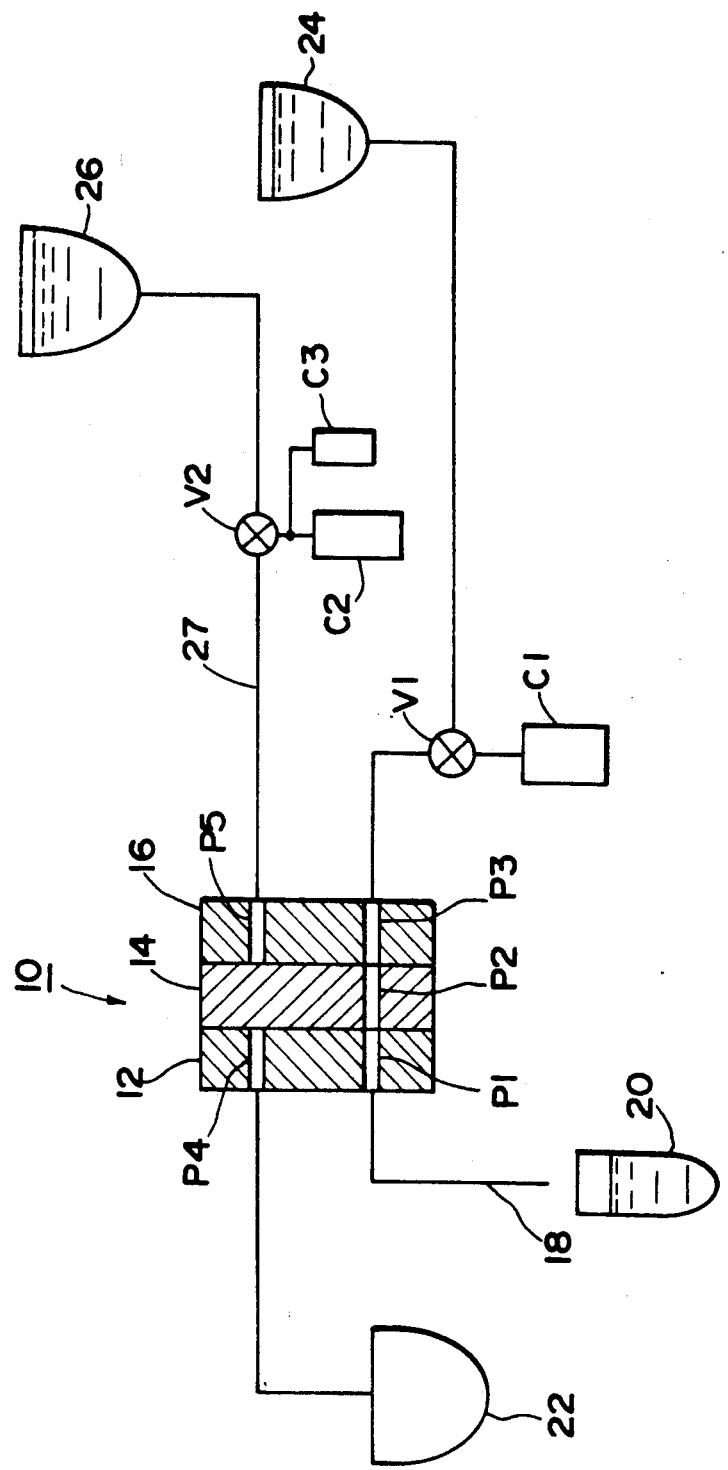
FIG. 3 is a schematic diagram showing an embodiment of an apparatus for diluting and mixing specimen according to one embodiment of the invention.

FIG. 3 is a schematic diagram showing an apparatus of this embodiment. The embodiment improves a conventional apparatus, in which a second reagent discharge means C3 such as a syringe (hereinafter called second syringe C3) is disposed parallel to a reagent discharge means C2 such as a syringe (hereinafter called first syringe C2). A reagent discharge volume (S1) of the first syringe C2 is, for example, 2.9 ml, and a reagent discharge volume (S2) of the second syringe C3 is, for example, 0.1 ml. The sum is 3.0 ml. The rate of the discharge (S2) of the second syringe C3 in the total discharge (S=S1+S2) is very slight. The second discharge volume (S2) may be enough as far as the specimen determined in the passage P2 for determination of the sampling valve 10 to force it out of the sampling valve 10. In the specimen transfer route (from the sampling valve 10 to the reaction vessel 22), since the passage of the sampling valve 10 is the narrowest, while the liquid specimen flows in this passage, a large fluid pressure is generated in the passage which applies a large stress on the specimen.

Figure 4:
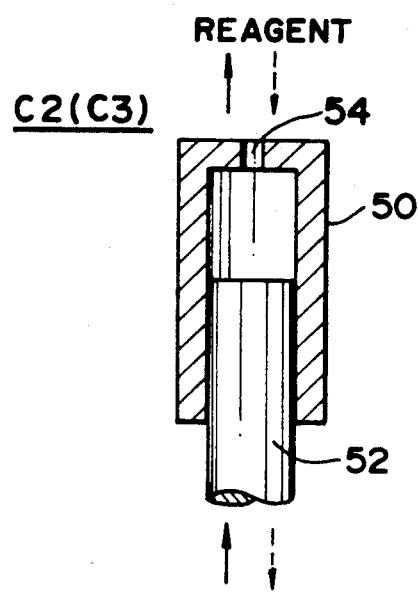
FIG. 4 is a sectional view showing an example of the reagent discharge means of FIG. 3.

FIG. 4 shows an example of the syringes C2, C3. The syringes C2, C3 comprise a cylinder 50 and a piston 52 sliding in the cylinder. By the vertical motion of the piston 52, the reagent is discharged from the tiny hole 54 in the upper part of the cylinder or the reagent is sucked in.

This embodiment is designed for slow discharge when the specimen passes through the narrow passage, and discharge at usual speed when passing through wide passages. Accordingly, in the construction shown in FIG. 3, first the second syringe C3 is operated in a discharge action, then the first syringe C2 is operated in a discharge action.

Figure 5:
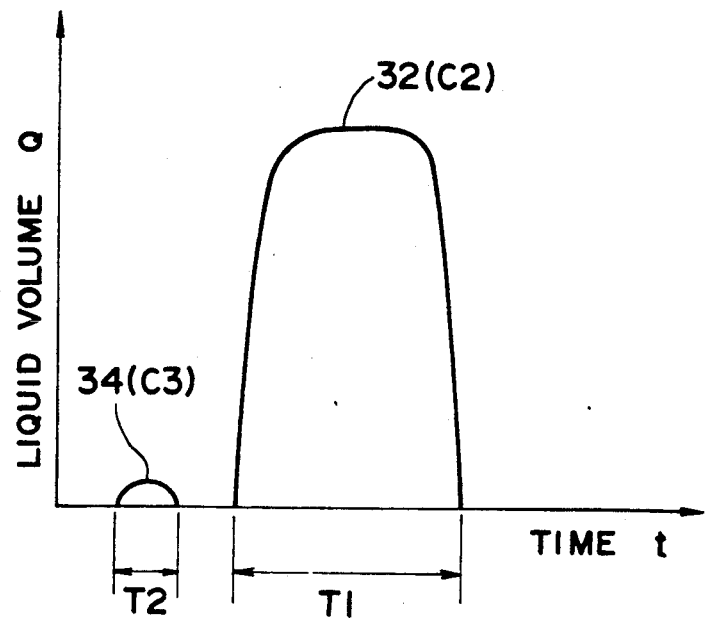
FIG. 5 is a curve showing the relationship of discharge time and discharge volume, representing the operation of the first reagent discharge means and second reagent discharge means of FIG. 3.

FIG. 5 is a diagram which explains the operation of the first and second syringes. Numerals 32, 34 are curves showing the discharge volume of the first and second syringes, respectively. Supposing the discharge action time of the first syringe C2 is T1 and the discharge action time of the second syringe C3 is T2, the durations of operations are set so as to satisfy the relationship of $(S2/T2) < (S1/T1)$. By such a setting, the second discharge flow becomes smaller than the first discharge flow, so that the liquid flows slowly during operation of the second syringe C3.

The specimen thus determined in the sampling valve 10 is discharged at low speed up to the exit of the sampling valve 10, and is discharged at usual speed thereafter.

EMBODIMENT 2

Figure 6:
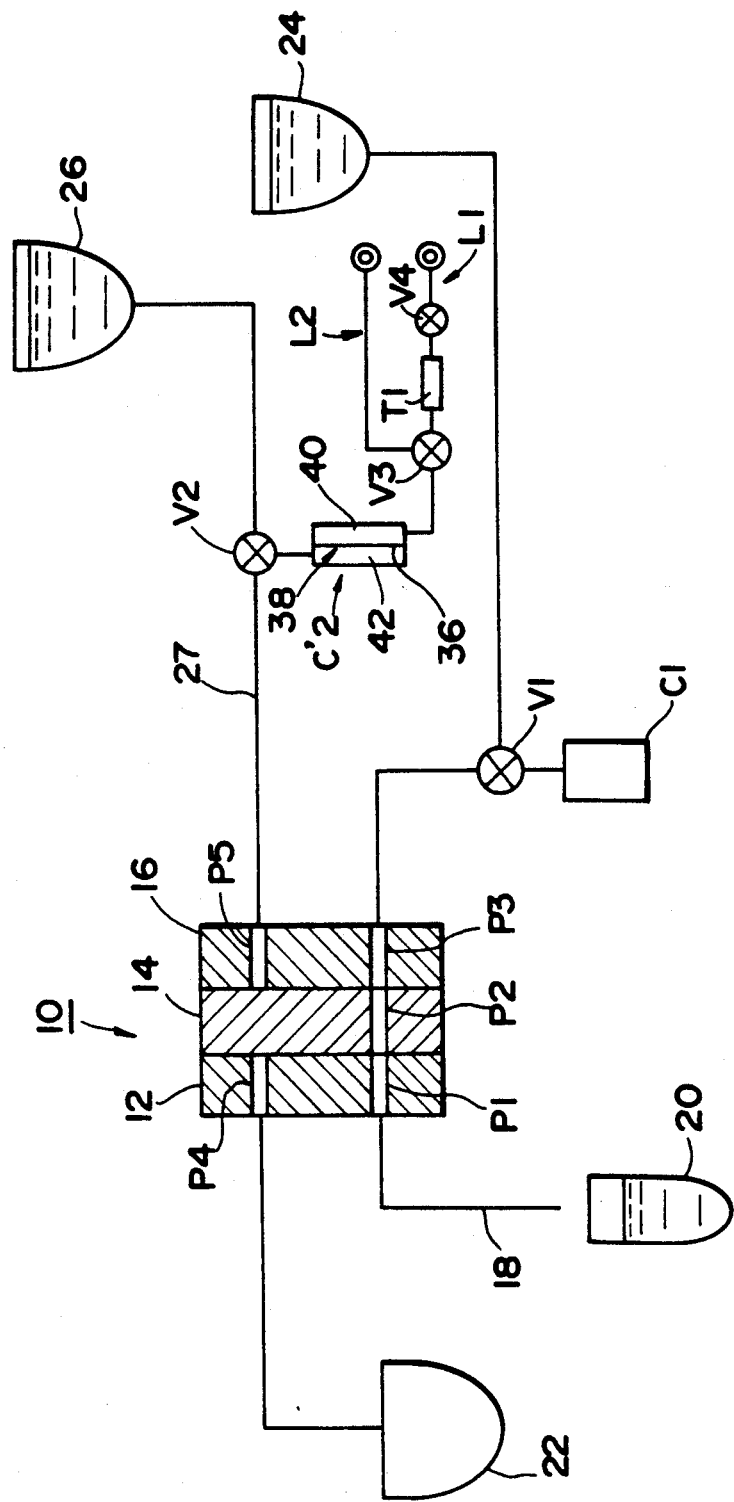
FIG. 6 is a schematic diagram showing another embodiment of an apparatus for diluting and mixing specimen of the invention.
Figure 7:
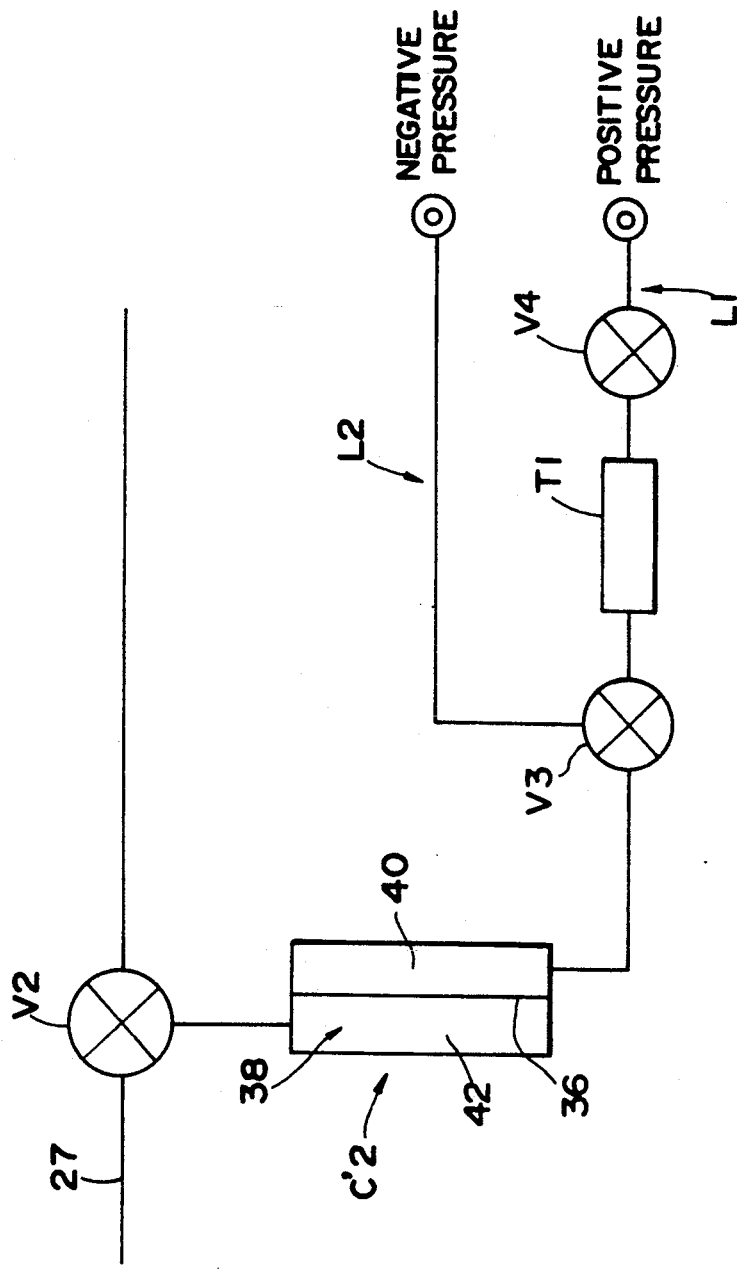

FIG. 6 and FIG. 7 are schematic diagrams of the apparatus of this embodiment. The reagent discharge means is a pump C'2 possessing a working chamber 38 separated into an air chamber 40 and a liquid chamber 42 by means of a thin film 36 such as a diaphragm. The construction comprises a three-way changeover valve V3 connected to the air chamber 40, a positive pressure supply line L1 connected to the three-way changeover valve V3, a negative pressure supply line L2 connected to the three-way changeover valve V3, a small volume part T1 and a valve V4 disposed in the positive pressure supply line L1. The liquid chamber 42 is connected to the valve V2.

In this way, the working chamber 38 is separated into the air chamber 40 and liquid chamber 42 by the thin film 36, and positive pressure and negative pressure are supplied into the air chamber 40 by changing over through the three-way changeover valve V3. By supplying positive pressure or negative pressure to the air chamber 40, the thin film 36 is deformed, and the volume of the liquid chamber 42 varies, so that a specific volume of liquid may be sucked in or discharged.

Besides, the small volume part T1 is installed between the three-way changeover valve V3 of the positive pressure supply line L1 and the valve V4, and by opening the valve V4, the small volume part T1 is brought into communication with the positive pressure source, and by closing the valve V4, the small volume part T1 is isolated from the positive pressure source.

The volume of the small volume part T1 may only be enough to operate the thin film, and a small volume tank or an enlarged part may be used; or a connection tube or a connection pipe only may be used.

Figure 8:
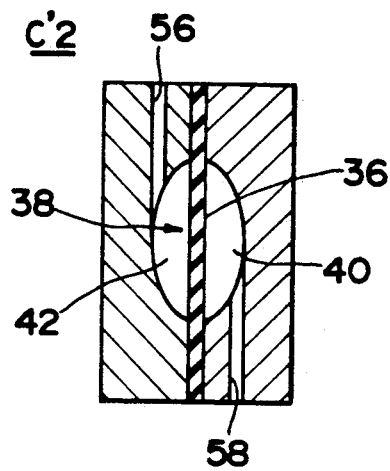
Figure 9:
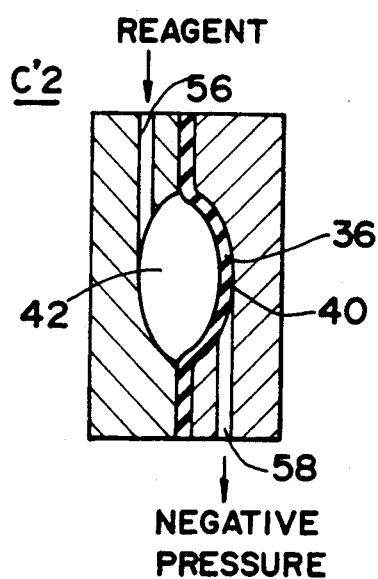
FIG. 9 shows a reagent suction state.
Figure 10:
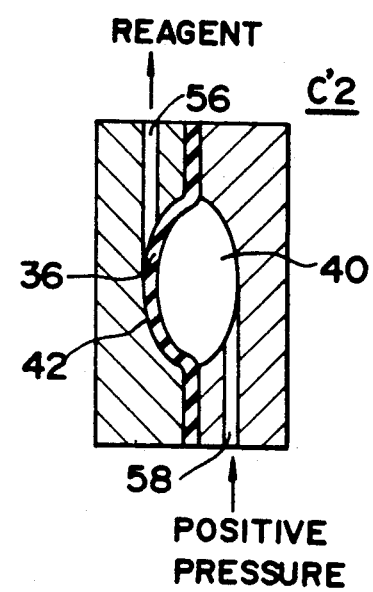
FIG. 10 shows a reagent discharge state.

FIG. 8 to FIG. 10 relate to an example of the pump C'2. Numeral 56 is a passage communicating with the liquid chamber 42, and 58 is a passage communicating with the air chamber 40. When an operating force is not applied in the passage 58, the thin film 36 is not deformed as shown in FIG. 8, and the reagent does not come in or go out from the passage 56. When a negative pressure is applied in the passage 58, that is, when the air in the air chamber 40 is purged out, the thin film 36 is deformed to the right side as shown in FIG. 9, and the reagent flows into the liquid chamber 42. When a positive pressure is applied in the passage 58, that is, when air is sent into the air chamber 40, the thin film 36 is deformed to the left side as shown in FIG. 10, and the reagent is discharged from the passage 56.

Figure 11:
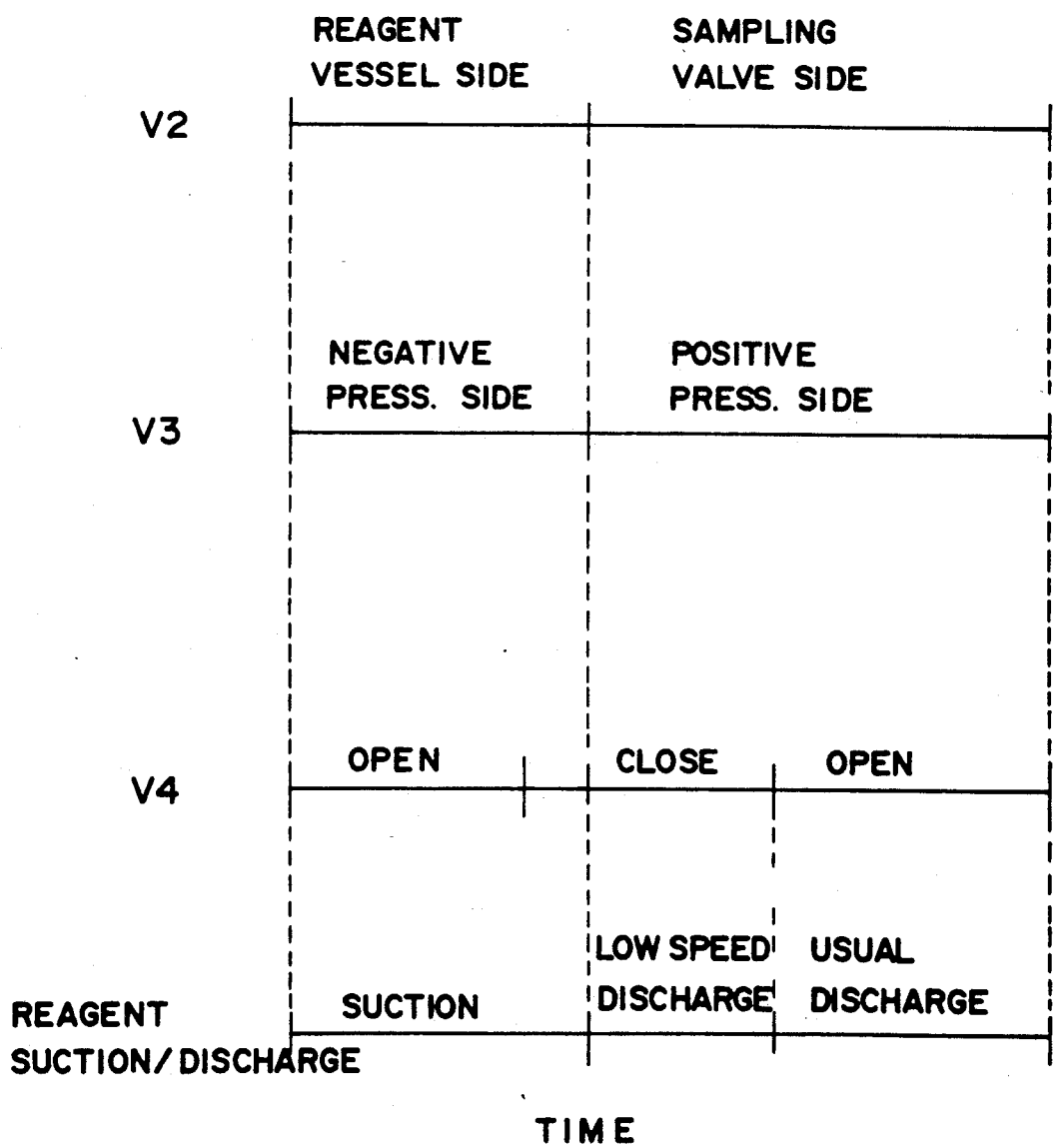
FIG. 11 is a time chart for explaining the suction and discharge state of the reagent discharge means C'2 as well as the operating state of the valves V2, V3, V4 of the apparatus shown in FIG. 6.

Referring next to FIG. 11, the operating state of the valves V2, V3, V4 and the suction and discharge state of the pump C'2 are explained.

Usually, the three-way changeover valve V3 is connected so that the driving pressure of the pump C'2 may be a negative pressure. At this time, the valve V2 is changed over so that the reagent may be drawn into the liquid chamber 42 of the pump C'2 from the reagent vessel 26. In this case, the valve V4 is open, and the small volume part T1 is in a positive pressure state.

Before the discharge action, the valve V4 is closed so that the positive pressure may not be directly applied to the pump C'2, and the valves V2, V3 are changed over, so that the valve V2 may communicate with the sampling valve 10, and so that the air chamber 40 and the small volume part T1 may communicate with each other through the valve V3, thereby entering into the initial discharge action. After the initial discharge action, the valve V4 is opened, and the usual discharge is done by consuming all the liquid remaining in the pump C'2.

The other construction and function of this embodiment are the same as in Embodiment 1.

Being thus constructed, the invention brings about the following effects.

(1) The specimen flows slowly in the narrow passage, and at a usual speed in wide passages. Accordingly, without damaging the specimen, the specimen and reagent may be mixed in a short time, and the processing capacity of the apparatus will not be lowered.

(2) In the apparatus, only one reagent discharge means is needed, and the cost may be reduced accordingly. Meanwhile, in order to keep the total discharge volume S, constant both discharge volumes S1, S2 of the discharge means C2, C3 must be uniform. Since there is only one discharge means, the total discharge is uniform. It may be considered that the ratio of the slow discharge and usual discharge may fluctuate somewhat, but it does not matter practically. Thus, the total discharge volume may be easily controlled uniformly.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method for diluting and mixing a liquid specimen for preparing a mixed solution of the liquid specimen and a reagent at a specific ratio, using a sampling valve, the method comprising the steps of:
   shifting the sampling valve to a suction mode and aspirating a specific volume of liquid specimen into the sampling valve;
   shifting the sampling valve to a delivery mode; and
   discharging the liquid specimen from the sampling valve by an initial pulse of a predetermined reagent volume until the liquid specimen is out of the sampling valve and thereafter by a further pulse, wherein the flow rate associated with the further pulse is greater than the flow rate associated with the initial pulse.

* * * * *